US00PP14425P29

(12) United States Plant Patent
Repp

(10) Patent No.: US PP14,425 P2
(45) Date of Patent: Dec. 30, 2003

(54) COLEUS PLANT NAMED 'PLUM GOOD'

(50) Latin Name: *Coleus×hybrida*
Varietal Denomination: Plum Good

(76) Inventor: Ralph Repp, 423 Country Rd., Waynesville, NC (US) 28785

( * ) Notice: Subject to any disclaimer, the term of this patent is extended or adjusted under 35 U.S.C. 154(b) by 0 days.

(21) Appl. No.: 10/291,005

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Coleus plant named 'Plum Good', characterized by its low-growing and outwardly spreading plant habit; and dark burgundy and bright purple bi-colored leaves with gold-colored leaf margins.

1 Drawing Sheet

Botanical classification/cultivar designation: *Coleus×hybrida* cultivar Plum Good.

BACKGROUND OF THE INVENTION

The present Invention relates to a new and distinct cultivar of Coleus plant, botanically known as *Solenostemon scutellarioides,* and hereinafter referred to by the cultivar name Plum Good.

The new cultivar was discovered by the Inventor in a controlled environment in Waynesville, N.C. as a naturally-occurring branch mutation of a selection of *Solenostemon scutellarioides* identified as trailing red, not patented. The new Coleus was observed within a population of plants of the trailing red selection in June, 2000. This branch mutation was selected on the basis of its unique leaf coloration.

Asexual reproduction of the new cultivar by terminal cuttings taken in Waynesville, N.C. since September, 2000, has shown that the unique features of this new Coleus are stable and reproduced true to type in successive generations.

SUMMARY OF THE INVENTION

Plants of the cultivar Plum Good have not been observed under all possible environmental conditions. The phenotype may vary somewhat with variations in environment such as temperature and light intensity without, however, any variance in genotype.

The following traits have been repeatedly observed and are determined to be the unique characteristics of 'Plum Good'. These characteristics in combination distinguish 'Plum Good' as a new and distinct cultivar:

1. Low-growing and outwardly spreading plant habit.
2. Dark burgundy and bright purple bi-colored leaves with gold-colored leaf margins.

Plants of the new Coleus are most similar to plants of the parent, the selection identified as trailing red. Plants of the new Coleus differ from plants of the parent selection primarily in foliage color as plants of the female selection have solid dark purple-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Coleus.

The photograph at the top of the sheet comprises a side perspective view of typical plant of 'Plum Good' grown in a container.

The photograph at the bottom of the sheet comprises a close-up view of typical leaves of 'Plum Good'.

DETAILED BOTANICAL DESCRIPTION

The cultivar Plum Good has not been observed under all possible environmental conditions. The phenotype may vary somewhat with variations in environment such as temperature and light intensity without, however, any variance in genotype.

The aforementioned photographs, following observations and measurements describe plants grown during the winter and spring in Encinitas, Calif., in an outdoor nursery and under conditions which approximate commercial production cultural and environmental conditions. Plants were about ten weeks from cuttings and were grown in one-gallon containers. During the production of the plants, day temperatures averaged 24° C. and night temperatures averaged 19° C.

In the following description, color references are made to The Royal Horticultural Society Colour Chart, 1995 Edition, except where general terms of ordinary dictionary significance are used.

Botanical classification: *Solenostemon scutellarioides* cultivar Plum Good.

Parentage: Naturally-occurring branch mutation of a selection of *Solensotemon scutellarioides,* not patented.

Propagation:

*Type cutting.*—Terminal cuttings.

*Time to initiate roots.*—Summer: About 7 days at 20° C. Winter: About 9 days at 20° C.

*Time to develop roots.*—Summer: About 18 days at 20° C. Winter: About 20 days at 20° C.

*Root description.*—Fine, fibrous, white in color.

*Rooting habit.*—Freely branching.

Plant description:

*Form.*—Annual flowering plant; low-growing, mounded and outwardly spreading. Moderate to rapid growth rate.

*Plant height.*—About 30 cm.

*Plant diameter.*—About 68 cm.

*Branching habit.*—Freely branching with potentially two lateral branches forming at every node.

*Lateral branches.*—Length: About 40 cm. Diameter: About 7 mm. Internode length: About 4 to 6 cm. Shape, in cross-section: Squarish. Texture: Pubescent. Color: 183A.

*Foliage description.*—Arrangement: Opposite; simple. Length: About 5.5 cm. Width: About 5 cm. Shape: Deltoid. Apex: Acute. Base: Truncate. Margin: Dentate to crenate. Texture, upper and lower surfaces: Pubescent; velvety. Venation pattern: Pinnate. Color: Young foliage, upper surface: 187A. Young foliage, lower surface: 187C. Fully expanded foliage, upper surface: Center, 187A; towards the margin, brighter than 61A; at margin, 161C. Fully expanded foliage, lower surface: Center, more gray than 187A; towards the margin, more gray than 187C. Venation, upper surface: 185C. Venation, lower surface: 185D. Petiole length: About 4 mm. Petiole diameter: About 2 mm. Petiole color: 183B.

Flower description: Flower development has not been observed.

Disease/pest resistance: Plants of the new Coleus have not been noted to be resistant to pathogens or pests common to Coleus.

Temperature tolerance: Plants of the new Coleus have been observed to tolerate temperatures from 2 to 35° C.

It is claimed:

1. A new and distinct cultivar of Coleus plant named 'Plum Good', as illustrated and described.

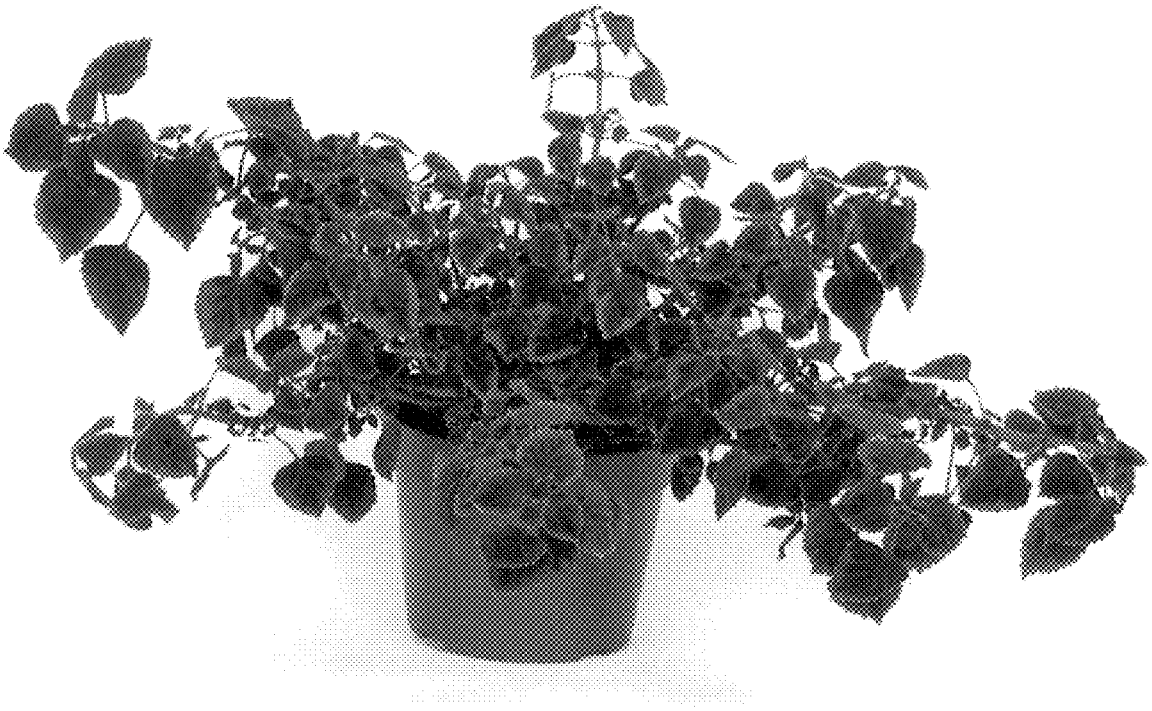
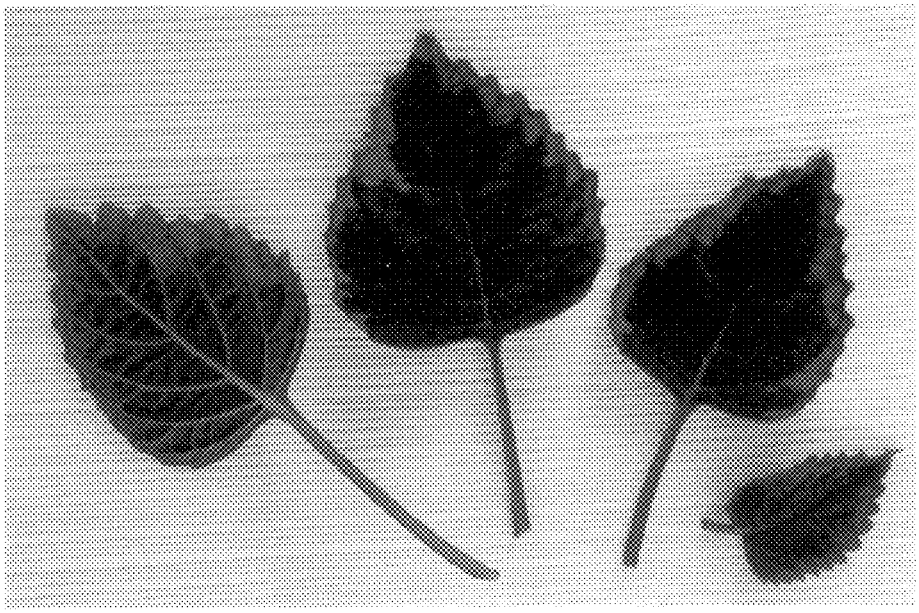

* * * * *